United States Patent
Kageyama

(10) Patent No.: US 9,201,296 B2
(45) Date of Patent: Dec. 1, 2015

(54) VERIFICATION AND MODIFICATION METHOD OF RULES OF DO-NOT-INSPECT REGIONS, COMPUTER PROGRAM, AND APPARATUS FOR SUCH VERIFICATION AND MODIFICATION

(75) Inventor: Kiyoshi Kageyama, Kashiwa (JP)

(73) Assignee: TOPPAN PRINTING CO., LTD., Tokyo (JP)

(*) Notice: Subject to any disclaimer, the term of this patent is extended or adjusted under 35 U.S.C. 154(b) by 1020 days.

(21) Appl. No.: 12/926,496

(22) Filed: Nov. 22, 2010

(65) Prior Publication Data
US 2011/0071783 A1 Mar. 24, 2011

(30) Foreign Application Priority Data
May 22, 2008 (JP) .............................. P2008-134173

(51) Int. Cl.
  *G06F 19/00* (2011.01)
  *G03F 1/84* (2012.01)
  *G01N 21/956* (2006.01)

(52) U.S. Cl.
  CPC ........ *G03F 1/84* (2013.01); *G01N 2021/95676* (2013.01)

(58) Field of Classification Search
  USPC ............................................. 702/83
  See application file for complete search history.

(56) References Cited

U.S. PATENT DOCUMENTS

| 2007/0050163 A1* | 3/2007 | Badger et al. .............. 702/83 |
| 2007/0070334 A1 | 3/2007 | Ogawa et al. |
| 2007/0237384 A1 | 10/2007 | Bruce et al. |
| 2011/0071783 A1* | 3/2011 | Kageyama ................... 702/83 |

FOREIGN PATENT DOCUMENTS

| JP | 5-198641 | 8/1993 |
| JP | 2004-191297 | 7/2004 |
| JP | 2006-119019 | 5/2006 |
| JP | 2009-42055 | 2/2009 |
| TW | 539916 | 7/2003 |
| TW | 200418092 | 9/2004 |
| WO | WO 2009/002340 A1 | 12/2008 |

OTHER PUBLICATIONS

Wayne Ruch, "Rules for DNIR Placement in TERA Format Database SLF Series and 5XX Series," Applications Note AN4084, KLA-Tencor Corporation, Aug. 2, 2002, 2pp.
International Search Report for PCT/JP2009/059053, mailed Aug. 2009.
Taiwanese Office Action mailed Jan. 8, 2014 in corresponding Taiwanese Application No. 098116374.

* cited by examiner

*Primary Examiner* — Tung S Lau

(57) ABSTRACT

A verification method and apparatus for do-not-inspect region rules include storing information specifying do-not-inspect regions, and storing a pixel unit size which defines a length of a single pixel unit. A minimum size verification process includes calculating sizes of do-not-inspect regions, and verifying whether a minimum size rule is obeyed, the minimum size rule requiring that a size of a do-not-inspect region is equal to or greater than a single pixel unit size while referring to the stored pixel unit size. A distance verification process includes calculating distances between pairs of do-not-inspect regions from among the do-not-inspect regions, and verifying whether a distance rule is obeyed, the distance rule requiring that the distance is in a range of greater than zero and less than a predetermined distance.

3 Claims, 7 Drawing Sheets

| INDEX | X COORDINATE OF LOWER LEFT CORNER | Y COORDINATE OF LOWER LEFT CORNER | X COORDINATE OF UPPER RIGHT CORNER | Y COORDINATE OF UPPER RIGHT CORNER | |
|---|---|---|---|---|---|
| 1 | 0 | 0 | 5000 | 20000 | ← A |
| 2 | 0 | 20000 | 28000 | 24000 | ← B |
| 3 | 0 | 24000 | 8000 | 40000 | ← C |

FIG. 1
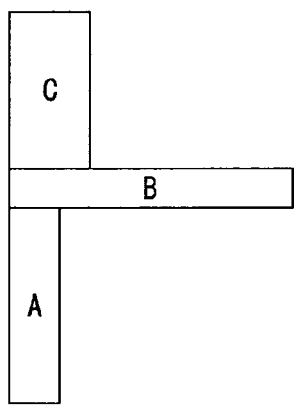
FIG. 2
| INDEX | X COORDINATE OF LOWER LEFT CORNER | Y COORDINATE OF LOWER LEFT CORNER | X COORDINATE OF UPPER RIGHT CORNER | Y COORDINATE OF UPPER RIGHT CORNER | |
|---|---|---|---|---|---|
| 1 | 0 | 0 | 5000 | 20000 | ← A |
| 2 | 0 | 20000 | 28000 | 24000 | ← B |
| 3 | 0 | 24000 | 8000 | 40000 | ← C |
FIG. 3
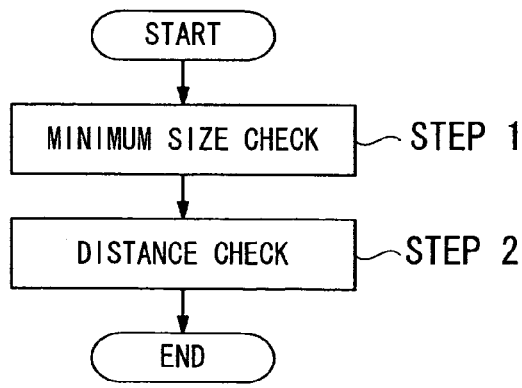

| INDEX | X COORDINATE OF LOWER LEFT CORNER | Y COORDINATE OF LOWER LEFT CORNER | X COORDINATE OF UPPER RIGHT CORNER | Y COORDINATE OF UPPER RIGHT CORNER | |
|---|---|---|---|---|---|
| 1 | 0 | 0 | 5000 | 24000 | ← A |
| 2 | 0 | 20000 | 28000 | 24000 | ← B |
| 3 | 0 | 24000 | 8000 | 40000 | ← C |

☐ REGION INTENDED TO BE DNIR
▨ REGIONS INTENDED NOT TO BE DNIR

☐ REGION INTENDED TO BE DNIR
▨ REGIONS INTENDED NOT TO BE DNIR
⬚ REGIONS DEFINED TO BE DNIRS

☐ REGION INTENDED TO BE DNIR
▨ REGIONS INTENDED NOT TO BE DNIR
⬚ REGIONS DEFINED TO BE DNIRS

VERIFICATION AND MODIFICATION METHOD OF RULES OF DO-NOT-INSPECT REGIONS, COMPUTER PROGRAM, AND APPARATUS FOR SUCH VERIFICATION AND MODIFICATION

CROSS REFERENCE TO RELATED APPLICATIONS

This application is a continuation application, under 35 U.S.C. §111(a), of international application no. PCT/JP2009/059053, filed on May 15, 2009, which claimed priority to Japanese application no. 2008-134173, filed on May 22, 2008, the disclosures of which are incorporated herein by reference.

TECHNICAL FIELD

The present invention relates to a technique for verifying rules for do-not-inspect regions (DNIRs) in a mask defect inspection system, and modifying DNIRs when the rule is violated.

BACKGROUND ART

Generally, during the inspection of defects in photomasks for optical lithography in a mask defect inspection system, false defects may be induced as a result of a trade-off with calibration (for example, refer to a paragraph [0018] of Patent Document 1). Here, the term "false defect" means a non-defective element that is erroneously determined to be defective by the mask defect inspection system.

Usually, circuits are designed at a manufacturable level. Important portions in which the circuits are designed at a manufacturable level are subject to calibration in a mask defect inspection system to avoid induction of false defects.

In some cases, however, patterns exceeding, for example, a certain processing limitation may be included in a photomask in order to evaluate such some processing limitations. Such patterns would experience extraordinarily poor pattern fidelity and are not satisfactorily calibrated. As a result, false defects are induced therein.

Too many false defects interrupt the operation of the mask defect inspection system. To avoid this, mask rule check (MRC) determines regions in which a large number of false defects are expected. In order to exclude the regions determined by the MRC from the inspection range, Do-Not-Inspect-Regions (DNIRs) are defined. The DNIRs are rectangular in shape.

When a plurality of DNIRs are to be defined, DNIR placement rule 1 to 5 must be obeyed (refer to Non-patent Document 1).

1. The minimum size of a DNIR is a single pixel. The pixel is a unit used in a mask defect inspection system. The length of the pixel is 125 nm, 90 nm, 72 nm or the like depending on the device or setting. The length of each pixel is also referred to as pixel size.
2. The number of DNIRs is not limited.
3. Some DNIRs may overlap with each other, and the overlapping area may be as small as it possibly be.
4. Some DNIRs may be in contact with each other by their edges.
5. If a pair of DNIRs neither overlap nor are in contact with each other, i.e., if the distance between the pair of DNIRs is not zero, the pair of DNIRs must be separated from each other by at least 128 pixels.

When a plurality of DNIRs is defined, if the DNIR placement rules are violated, an operation of the mask defect inspection system will sets off a DNIR placement rule error.

It is preferable that the size of the DNIR in the mask defect inspection system is as small as possible. However, a DNIR can be represented only by a rectangular area. When DNIRs are to be defined for a photomask illustrated in FIG. 14, for example, one DNIR may simply be defined as illustrated in FIG. 15. However, regions intended to be inspected are also included in this placement of DNIR. This problem can be solved by defining DNIRs as illustrated in FIG. 16 to reduce the size of the DNIRs. However, in this case, DNIR placement rule described above must be obeyed. When a plurality of DNIRs as illustrated in FIG. 16 are required in a photomask, conventionally, an operator has not been able to check the existence of the DNIR placement rule violation without operating the mask defect inspection system.

RELATED ART DOCUMENTS

Patent Document

[Patent Document 1] Japanese Unexamined Patent Application, First Publication No. 2004-191297

Non-Patent Document

[Non-patent Document 1] Wayne Ruch, "Rules for DNIR Placement in TERA Format Database SLF Series and 5XX Series" Application Note, USA, KLA-Tencor Corporation, Aug. 2, 2002, AN4084, p. 2

DISCLOSURE OF THE INVENTION

Problems to be Solved by the Invention

The present invention was made in view of the above-mentioned circumstances, and an object thereof is to verify the existence of a violation of DNIR placement rule without operating the mask defect inspection system, by analyzing DNIR information of the mask defect inspection system, and properly implement a photomask defect inspection process in the mask defect inspection system using modified DNIR information.

Means for Solving the Problems (1) In order to solve the aforementioned problem, one aspect of the present invention employs a verification method of do-not-inspect region rules, the method including: an information storage process which includes storing information of a plurality of do-not-inspect regions which specifies each of the plurality of do-not-inspect regions, and storing a pixel size which defines a length of a single pixel; a minimum size verification process which includes, calculating a size of each of the plurality of do-not-inspect regions, and verifying whether a minimum size rule is obeyed, the minimum size rule requiring that the size of each of the plurality of do-not-inspect regions is equal to or greater than a single unit of the pixel size while referring to the pixel size; and a distance verification process which includes, calculating distances between every pair among the plurality of do-not-inspect regions by referring to the information of the plurality of do-not-inspect regions, and verifying whether a distance rule is obeyed when a distance between a pair among the plurality of do-not-inspect regions is greater than zero, the distance rule requiring that the distance is equal to or greater than a predetermined distance.

(2) The verification method of do-not-inspect region rules may be implemented in the following manner: the method may further include a modification process which includes, when it is determined in the distance verification process that the distance rule is violated, modifying one of the pair of do-not-inspect regions violating the distance rule, so that sides of the pair of the do-not-inspect regions contact with each other.

(3) The verification method of do-not-inspect region rules may be implemented in the following manner: in the modification process, a shorter one of the sides of the pair of the do-not-inspect regions is moved to a position where it contacts a longer one of the sides.

(4) In order to solve the aforementioned problem, one aspect of the present invention employs a verification program of do-not-inspect region rules, the program causing a computer to execute: an information storage routine which includes storing information of a plurality of do-not-inspect regions which specifies each of the plurality of do-not-inspect regions, and storing a pixel size which defines a length of a single pixel; a minimum size verification routine which includes, calculating a size of each of the plurality of do-not-inspect regions, and verifying whether a minimum size rule is obeyed, the minimum size rule requiring that the size of each of the plurality of do-not-inspect regions is equal to or greater than a single unit of the pixel size while referring to the pixel size; and a distance verification routine which includes, calculating distances between every pair among the plurality of do-not-inspect regions while referring to the information of the plurality of do-not-inspect regions, and verifying whether a distance rule is obeyed, the distance rule requiring that when a distance between a pair among the plurality of do-not-inspect regions is greater than zero, the distance is greater than a predetermined distance.

(5) The above-described verification program of do-not-inspect region rules may be constituted as follows: the program further includes a modification routine which includes, when it is determined in the distance verification routine that the distance rule is violated, modifying any of the pair of do-not-inspect regions which violate the distance rule so that sides of the pair of the do-not-inspect regions touch each other.

(6) The above-described verification program of do-not-inspect region rules may be constituted as follows: in the modification routine, a side which is shorter among the sides of the pair of the do-not-inspect regions is displaced to a position to touch a side which is longer.

(7) In order to solve the aforementioned problem, one aspect of the present invention employs a verification apparatus of do-not-inspect region rules, the apparatus comprising: an information storage member which stores information of a plurality of do-not-inspect regions which specifies each of the plurality of do-not-inspect regions, and stores a pixel size which defines a length of a single pixel; a minimum size verification member which calculates a size of each of the plurality of do-not-inspect regions, and verifies whether a minimum size rule is obeyed, the minimum size rule requiring that the size of each of the plurality of do-not-inspect regions is equal to or greater than a single unit of the pixel size while referring to the pixel size; and a distance verification member which calculates distances between every pair among the plurality of do-not-inspect regions while referring to the information of the plurality of do-not-inspect regions, and verifies whether a distance rule is obeyed, the distance rule requiring that when a distance between a pair among the plurality of do-not-inspect regions is greater than zero, the distance is greater than a predetermined distance.

(8) The above-described verification apparatus of do-not-inspect region rules may be constituted as follows: the apparatus further includes a modification member which includes, when it is determined in the distance verification member that the distance rule is violated, modifying any of the pair of do-not-inspect regions which violate the distance rule so that sides of the pair of the do-not-inspect regions touch each other.

(9) The above-described inspection system for rules of do-not-inspect regions may be constituted as follows: in the modification member, a side which is shorter between the sides of the pair of the do-not-inspect regions is displaced to a position to touch a side which is longer.

Effect of the Invention

The inventions of above-described (1), (4) and (7) have an advantageous effect that the existence of a violation of DNIR placement rule can be verified without operating the mask defect inspection system, by analyzing DNIR information of the mask defect inspection system.

The inventions of above-described (2), (5) and (8) have the following advantageous effect: since the DNIR information is modified to remove the violation of DNIR placement rule, a photomask defect inspection process can be implemented properly in the mask defect inspection system by using the modified DNIR information.

The inventions of above-described (3), (6) and (9) have an effect of minimizing an increase in the area of the DNIRs during the modification.

BRIEF DESCRIPTION OF THE DRAWINGS

FIG. 1 illustrates exemplary placement of a plurality of do-not-inspect regions (DNIRs).

FIG. 2 illustrates exemplary DNIR information in the exemplary placements of the plurality of DNIRs illustrated in FIG. 1.

FIG. 3 is a flowchart illustrating an overall flow of the verification and modification method of DNIRs in a mask defect inspection system according to the present embodiment.

MODE FOR IMPLEMENTING THE INVENTION

Hereinafter, an embodiment of the present invention will be described.

In the present embodiment, do-not-inspect region (DNIR) information is an array which has, as components, XY coordinates of the lower left corner and XY coordinates of the upper right corner of each of placed DNIRs. Since a DNIR is rectangular in shape, the DNIR can be defined by the XY coordinates of the lower left corner and the XY coordinates of the upper right corner thereof.

For example, when the DNIRs A to C are placed as illustrated in FIG. 1, the DNIR information may become an array as shown in FIG. 2. In FIG. 2, the X coordinate of the lower left corner, the Y coordinate of the lower left corner, the X coordinate of an upper right corner and the Y coordinate of the upper right corner referred to by indices 1 to 3 each represents the X coordinate of the lower left corner, the Y coordinate of the lower left corner, the X coordinate of the upper right corner and the Y coordinate of the upper right corner of the DNIRs A to C.

This DNIR information and the pixel size used in the mask defect inspection system are stored in a memory in advance.

Using the DNIR information and the pixel size used in the mask defect inspection system, a minimum size check is performed in step 1 and a distance check is performed in step 2 as illustrated in a flowchart of FIG. 3.

Figure 4:
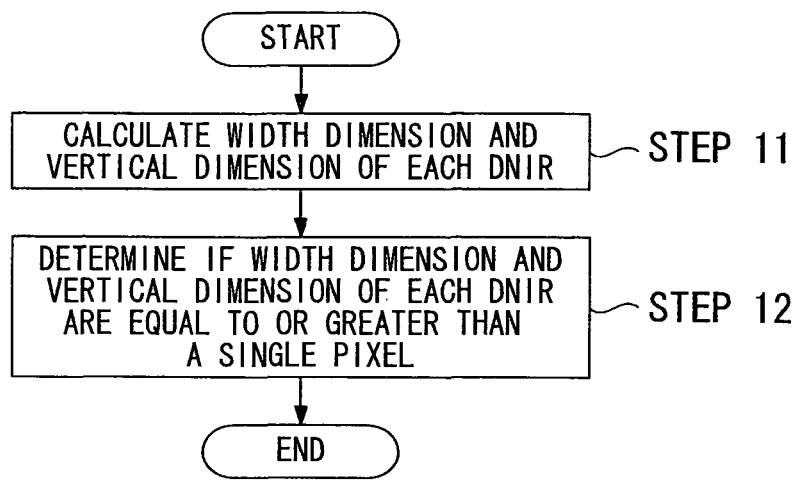
FIG. 4 is a flowchart illustrating a detailed flow of "minimum size check" of step 1.

Hereinafter, a detailed flow of the "minimum size check" of step 1 will be described with reference to a flowchart of FIG. 4.

Step 11:

First, XY coordinates of the lower left corner and XY coordinates of the upper right inspection region of each DNIR are read from the DNIR information, and the vertical dimension and the width dimension are calculated for each DNIR.

Step 12:

Next, it is determined if the width dimension and the vertical dimension of each DNIR is equal to or greater than a single pixel that is used in the mask defect inspection system.

Figure 5:
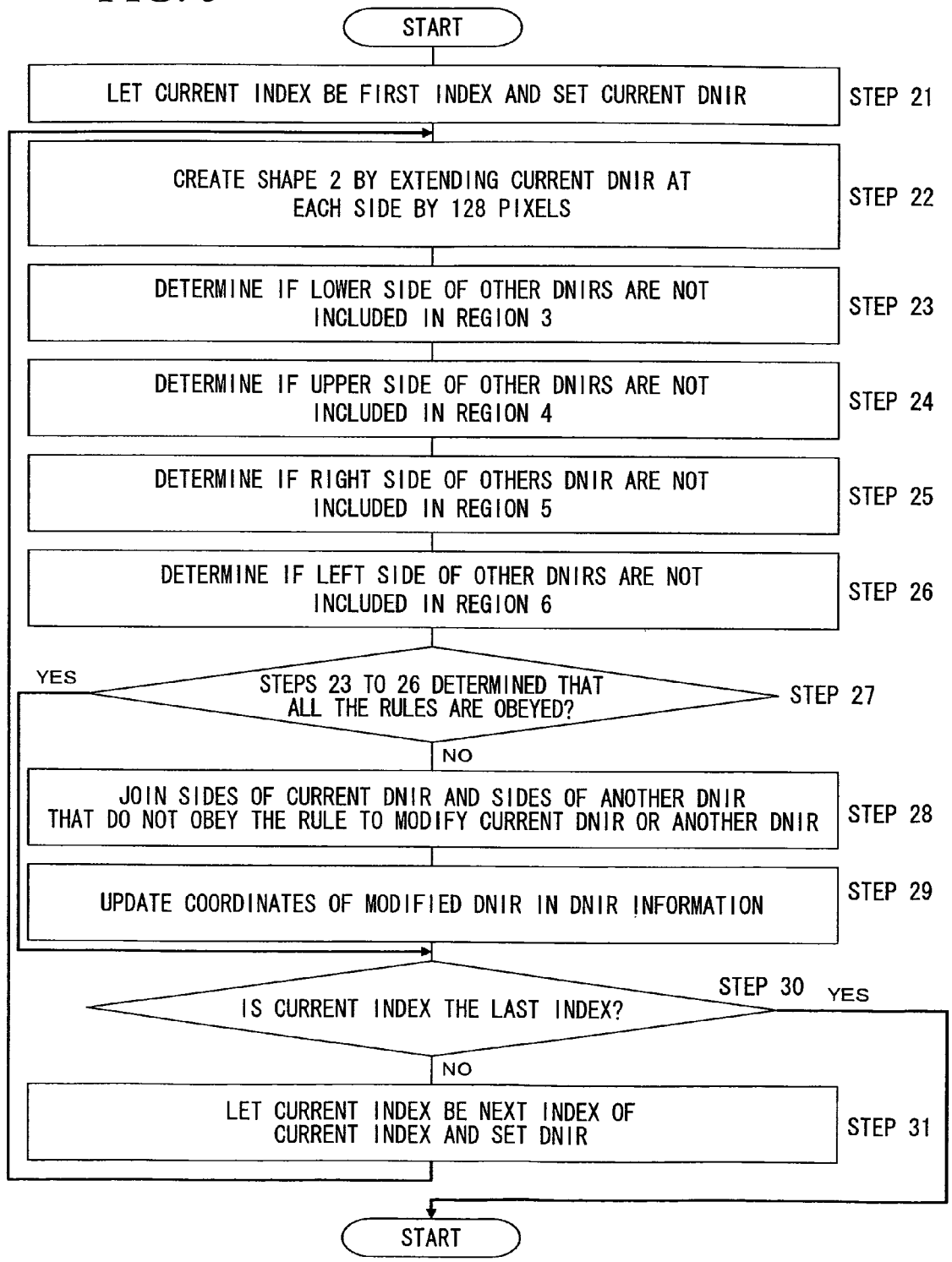
FIG. 5 is a flowchart illustrating a detailed flow of "distance check" of step 2.

Hereinafter, a detailed flow of the "distance check" of step 2 will be described with reference to a flowchart of FIG. 5.

Step 21:

The current index is set to be the first index, and the DNIR of which XY coordinates of the lower left corner and XY coordinates of the upper right corner are referred to by the current index is set to be the current DNIR.

Figure 6:
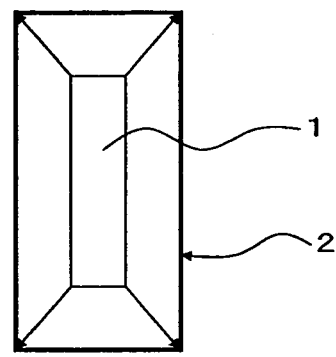
FIG. 6 illustrates a shape that is obtained by extending the current DNIR at each side by 128 pixels.

Step 22:

The XY coordinates of the lower left corner and the XY coordinates of the upper right corner of the current DNIR are obtained from the DNIR information using the current index. With reference to the pixel size, 128 pixels are subtracted from the XY coordinates of the lower left corner, and 128 pixels are added to the XY coordinates of the upper right corner of the current DNIR 1, as illustrated in FIG. 6. In this manner, a shape 2 is created that is enlarged from the current DNIR 1 at each side by 128 pixels.

Figure 7:
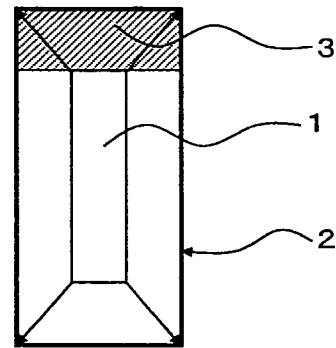
FIG. 7 illustrates a shape which represents a region within the extended shape located below an upper side of the extended shape and above an upper side of the current DNIR.

Step 23:

As illustrated in FIG. 7, by referring to the DNIR information, it is determined whether a rule is obeyed, which requiring that the lower side of any DNIR other than the current DNIR 1 is not included in the region 3 within the extended shape 2, the region 3 being below the upper side of the extended shape 2 and above the upper side of the current DNIR 1.

Figure 8:
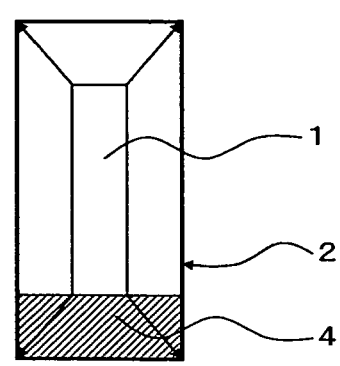
FIG. 8 illustrates a shape which represents a region within the extended shape located above a lower side of the extended shape and below a lower side of the current DNIR.

Step 24:

As illustrated in FIG. 8, by referring to the DNIR information, it is determined whether a rule is obeyed, which requiring that the upper side of any DNIR other than the current DNIR 1 is not included in the region 4 within the extended shape 2, the region 4 being above a lower side of the extended shape 2 and below the lower side of the current DNIR 1.

Figure 9:
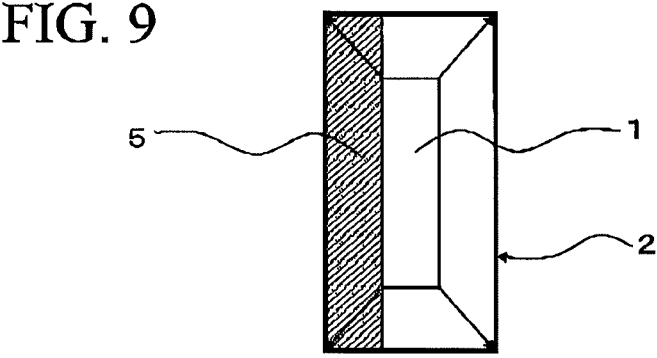
FIG. 9 illustrates a shape which represents a region within the extended shape located to the right of a left side of the extended shape and to the left of a left side of the current DNIR.

Step 25:

As illustrated in FIG. 9, by referring to the DNIR information, it is determined whether a rule is obeyed, which requiring that the right side of any DNIR other than the current DNIR 1 is not included in a region 5 within the extended shape 2, the region 5 begin to the right of a left side of the extended shape 2 and to the left of the left side of the current DNIR 1.

Figure 10:
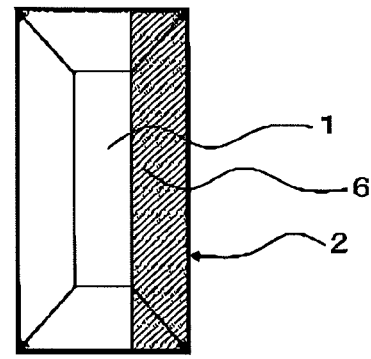
FIG. 10 illustrates a shape which represents a region within the extended shape located to the left of a right side of the extended shape and to the right of a right side of the current DNIR.

Step 26:

As illustrated in FIG. 10, by referring to the DNIR information, it is determined whether a rule is obeyed, which requiring that the left side of any DNIR other than the current DNIR 1 is not included in a region 6 within the extended shape 2, the region 6 being to the left of a right side of the extended shape 2 and to the right of the right side of the current DNIR 1 is obeyed.

Step 27:

If steps 23 to 26 determined that at least one of the rules is violated, the process proceeds to step 28; and if, on the other hand, steps 23 to 26 determined that all the rules are obeyed, the process proceeds to step 30.

Step 28:

For a combination of the current DNIR and another DNIR which do not follow the rules, a side of the current DNIR and a side of another DNIR are joined together to modify the current DNIR or the another DNIR. At this time, the shorter one of the sides is moved to join to the longer one of the sides, so as to minimize the area of the modified DNIR.

Figure 11:
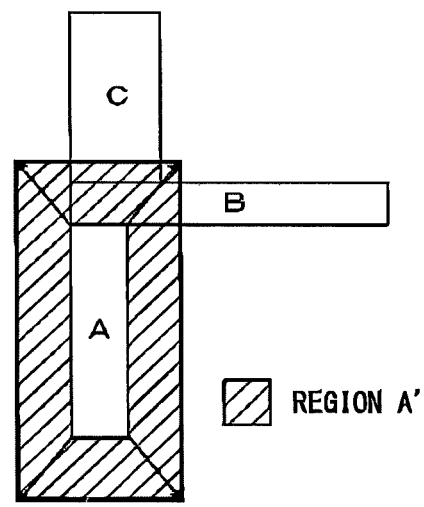
FIG. 11 illustrates a shape obtained by extending a DNIR A illustrated in FIG. 1 at each side by 128 pixels.

As an example, a case will be considered bellow, in which a DNIR A in FIG. 1 is set as the current DNIR, which is extended at its each side by 128 pixels to thereby obtain the shape (hereinafter, referred to as region A') as illustrated in FIG. 11.

Figures 12, 13:
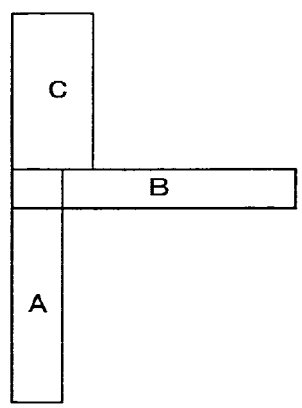
FIG. 12 illustrates an exemplary modification of the DNIRs illustrated in FIG. 1.
FIG. 13 illustrates updated information of the DNIR information of FIG. 2 updated through the modification of the DNIRs illustrated in FIG. 12.
Figure 14:
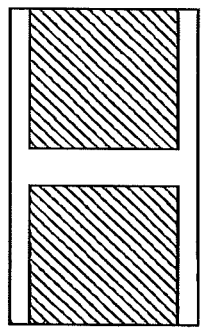
FIG. 14 illustrates an exemplary photomask.
Figure 15:
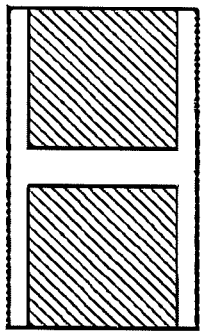
FIG. 15 illustrates an exemplary placement of a DNIR.
Figure 16:
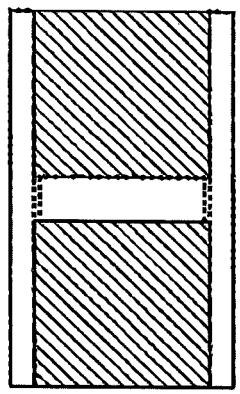
FIG. 16 illustrates an exemplary placement of DNIRs.

In this case, the lower side of a DNIR C is included in the region within the region A', below the upper side of the region A' and above the upper side of the DNIR A. In this case, since the upper side of the DNIR A is shorter than the lower side of the DNIR C, the DNIR A is extended upward from the upper side of the DNIR A until it joins to the lower side of the DNIR C, as illustrated in FIG. 12. With this procedure, the increase in the area of the DNIR A is smaller than an increase in the area of the DNIR C in a case in which the lower side of the DNIR C is extended downward and joined to the upper side of the DNIR A. Thus, an increase in the area of the modified DNIR is minimized.

Step 29:

In DNIR information, the original XY coordinates of the lower left corner and the upper right corner of the DNIR to be modified, is overwritten by the modified XY coordinates of the lower left corner and the upper right corner.

As an example, updated information of the DNIR information of FIG. 2 through the modification of the DNIRs as illustrated in FIG. 12 is shown in FIG. 13.

Step 30:

If the current index is the last index, the process proceeds to END; and if, on the other hand, the current index is not the last index, the process proceeds to step 31.

Step 31:

New current index is set to be the index subsequent to the current index. A new current DNIR is set to be the DNIR of which XY coordinates of the lower left corner and XY coordinates of the upper right corner are referred to by the new current index. The process then returns to step 22.

INDUSTRIAL APPLICABILITY

The invention of the present application has an effect that the existence of a violation of DNIR placement rule can be verified by analyzing DNIR information of the mask defect inspection system, without operating a mask defect inspection system.

REFERENCE NUMERALS

A: do-not-inspect region
B: do-not-inspect region
C: do-not-inspect region
1: current do-not-inspect region
2: the shape obtained by extending the current do-not-inspect region at each side by 128 pixels
3: region within extended shape located below the upper side of extended shape and above the upper side of current do-not-inspect region 1
4: region within extended shape located above lower side of extended shape and below lower side of current do-not-inspect region
5: region within extended shape located to the right of left side of extended shape and to the left of left side of current do-not-inspect region
6: region within extended shape located to the left of right side of extended shape and to the right of right side of current do-not-inspect region

The invention claimed is:

1. A method of inspecting a defect in a mask used in production of a circuit, the method comprising:
   executing by computer hardware implementing processes:
      calculating a width and a height of each of a plurality of rectangular shaped do-not-inspect regions of the mask based upon stored information specifying the do-not-inspect regions, and verifying whether a minimum size rule is obeyed, the minimum size rule requiring that the width and the height of a do-not-inspect region be equal to or greater than a width and a height of a single pixel unit;
      calculating distances between a pair of the do-not-inspect regions from among the do-not-inspect regions; and
      determining that a distance rule is violated when at least one of the distances between the pair of do-not-inspect regions is in a range of greater than zero and less than a determined distance, and modifying the pair of the do-not-inspect regions, the at least one of the distances between which are in the range, so that at least two sides of the pair of the do-not-inspect regions touch each other,
      wherein in a case where a longer side of two sides, which face each other, of the pair of the do-not-inspect regions is set to be a first do-not-inspect region, and a shorter side of the two sides of the pair of do-not-inspect regions is set to be a second do-not-inspect region, the second do-not-inspect region is extended such that the shorter side comes in contact with the longer side of the pair of do-not-inspect regions, thereby the pair of the do-not-inspect regions, the at least one of the distances between which are in the range, are modified so that modified sides of the pair of the do-not-inspect regions touch each other.

2. A non-transitory computer-readable medium storing a verification program of do-not-inspect region rules for a mask used in production of a circuit, the verification program causing a computer to execute:
   calculating a width and a height of each of a plurality of rectangular shaped do-not-inspect regions of the mask based upon stored information specifying the do-not-inspect regions, and verifying whether a minimum size rule is obeyed, the minimum size rule requiring that the width and the height of a do-not-inspect region be equal to or greater than a width and a height of a single pixel unit;
   calculating distances between a pair of the do-not-inspect regions from among the do-not-inspect regions; and
   determining that a distance rule is violated when at least one of the distances between the pair of do-not-inspect regions is in a range of greater than zero and less than a determined distance, and modifying the pair of the do-not-inspect regions, the at least one of the distances between which are in the range, so that at least two sides of the pair of the do-not-inspect regions touch each other,
   wherein in a case where a longer side of two sides, which face each other, of the pair of the do-not-inspect regions is set to be a first do-not-inspect region, and a shorter side of the two sides of the pair of do-not-inspect regions is set to be a second do-not-inspect region, the second do-not-inspect region is extended such that the shorter side comes in contact with the longer side of the pair of do-not-inspect regions, thereby the pair of the do-not-inspect regions, the at least one of the distances between which are in the range, are modified so that modified sides of the pair of the do-not-inspect regions touch each other.

3. A verification apparatus of do-not-inspect region rules for a mask used in production of a circuit, the verification apparatus comprising:
   an information storage storing information specifying a plurality of do-not-inspect regions, and a pixel unit size which defines a length of a single pixel unit;
   computer hardware implementing a process(es) that:
      calculates a width and a height of each of a plurality of rectangular shaped do-not-inspect regions of the mask based upon the stored information specifying the do-not-inspect regions, and verifies whether a minimum size rule is obeyed, the minimum size rule requiring that the width and the height of a do-not-inspect region be equal to or greater than a width and a height of the single pixel unit size;
      calculates distances between a pair of the do-not-inspect regions from among the do-not-inspect regions; and
      determines that a distance rule is violated when at least one of the distances between the pair of do-not-inspect regions is in a range of greater than zero and less than a determined distance, and modifies the pair of the do-not-inspect regions, the at least one of the distances between which are in the range, so that at least two sides of the pair of the do-not-inspect regions touch each other, wherein in a case where a longer side of two sides, which face each other, of the pair of the do-not-inspect regions is set to be a first do-not-inspect region, and a shorter side of the two sides of the pair of do-not-inspect regions is set to be a second do-not-inspect region, the second do-not-inspect region is extended such that the shorter side comes in contact with the longer side of the pair of do-not-inspect regions, thereby the pair of the do-not-inspect regions, the at least one of the distances between which are in the range, are modified so that modified sides of the pair of the do-not-inspect regions touch each other.

* * * * *